(12) United States Patent
Tanimoto et al.

(10) Patent No.: US 8,193,493 B2
(45) Date of Patent: Jun. 5, 2012

(54) CHARGED PARTICLE BEAM APPARATUS

(75) Inventors: Sayaka Tanimoto, Kodaira (JP); Hiroya Ohta, Kokubunji (JP); Hiroshi Makino, Kokubunji (JP); Ryuichi Funatsu, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/032,050

(22) Filed: Feb. 22, 2011

(65) Prior Publication Data
US 2011/0139985 A1      Jun. 16, 2011

Related U.S. Application Data

(63) Continuation of application No. 12/037,623, filed on Feb. 26, 2008, now Pat. No. 7,906,761.

(30) Foreign Application Priority Data

Mar. 2, 2007   (JP) ................................. 2007-052166

(51) Int. Cl.
   *G01N 23/00*    (2006.01)
   *G01N 23/225*   (2006.01)

(52) U.S. Cl. ........ 250/310; 250/306; 250/307; 250/311; 250/397

(58) Field of Classification Search .................. 250/306, 250/307, 310, 311, 397
See application file for complete search history.

(56) References Cited

U.S. PATENT DOCUMENTS

| | | | |
|---|---|---|---|
| 5,892,224 A * | 4/1999 | Nakasuji ...................... 250/310 |
| 6,844,550 B1 * | 1/2005 | Yin et al. ......................... 850/9 |
| 6,855,929 B2 | 2/2005 | Kimba et al. |
| 6,977,375 B2 * | 12/2005 | Yin et al. ......................... 850/6 |
| 7,276,707 B2 * | 10/2007 | Iwasaki et al. ............. 250/396 R |
| 7,378,668 B2 | 5/2008 | Tanimoto et al. |
| 7,385,197 B2 * | 6/2008 | Nakasuji et al. .............. 250/310 |
| 7,425,703 B2 * | 9/2008 | Nakasuji et al. .............. 250/310 |
| 7,521,676 B2 * | 4/2009 | Okuda et al. ................. 250/310 |
| 7,880,143 B2 * | 2/2011 | Tanimoto et al. ............. 250/310 |
| 7,906,761 B2 * | 3/2011 | Tanimoto et al. ............. 250/310 |
| 8,067,732 B2 * | 11/2011 | Nakasuji et al. .............. 250/311 |
| 2005/0214958 A1 | 9/2005 | Nakasuji et al. |
| 2005/0279936 A1 * | 12/2005 | Litman et al. ................. 250/310 |
| 2006/0016989 A1 * | 1/2006 | Nakasuji et al. .............. 250/310 |
| 2007/0194229 A1 * | 8/2007 | Okuda et al. ................. 250/310 |
| 2008/0067376 A1 | 3/2008 | Tanimoto et al. |
| 2011/0272576 A1 * | 11/2011 | Otaki et al. ................... 250/306 |

FOREIGN PATENT DOCUMENTS

JP        2007-317467       12/2007

* cited by examiner

*Primary Examiner* — David A Vanore
(74) *Attorney, Agent, or Firm* — Mattingly & Malur, PC (57) ABSTRACT

A charged particle beam apparatus that can achieve both high defect-detection sensitivity and high inspection speed for a sample with various properties in a multi-beam type semiconductor inspection apparatus. The allocation of the primary beam on the sample is made changeable, and furthermore, the beam allocation for performing the inspection at the optimum inspection specifications and at high speed is selected based on the property of the sample. In addition, many optical parameters and apparatus parameters are optimized. Furthermore, the properties of the selected primary beam are measured and adjusted.

10 Claims, 6 Drawing Sheets

ALLOCATION A

FIG. 2C

ALLOCATION B

FIG. 2D

ALLOCATION C

FIG. 2E

ALLOCATION D

CHARGED PARTICLE BEAM APPARATUS

This is a continuation application of U.S. application Ser. No. 12/037,623, filed Feb. 26, 2008, now allowed, the contents of which are hereby incorporated by reference into this application.

CLAIM OF PRIORITY

The present application claims priority from Japanese application JP 2007-052166 filed on Mar. 2, 2007, the content of which is hereby incorporated by reference into this application.

FIELD OF THE INVENTION

The present invention relates to an inspection apparatus and a measurement apparatus that are employed in a semiconductor process, more particularly, to a high speed and high precision charged particle beam apparatus.

BACKGROUND OF THE INVENTION

In the semiconductor process, a charged beam (hereinafter, referred to as primary beam) such as an electron beam or an ion beam is irradiated on a sample, and signals from a generated secondary charged beam (hereinafter, referred to as secondary beam) such as a secondary electron beam are acquired, wherein an electron beam length measurement apparatus that measures the shape and size of a pattern formed on the sample, and an electron beam inspection apparatus that inspect the existence or nonexistence of defects on the sample are employed.

In such a charged particle beam apparatus, enhancing the speed to process the sample, that is, enhancing the speed to inspect the sample is an important problem together with the enhancing the sensitivity to detect defects on the sample. In order to solve this problem, a multi-beam type charged particle beam apparatus in which plural beams is employed has been proposed. For example, in Japanese Patent Application No. 2006-144934, a multi-beam type charged particle beam apparatus is disclosed, wherein an electron beam emitted from a single electron gun is separated into plural beams, and the plurality of beams, which are formed individually by focusing lenses arranged like an array, are projected and scanned on the sample using a single optical element.

SUMMARY OF THE INVENTION

As mentioned above, by using the multi-beam type charged particle beam apparatus in which plural primary beams are scanned on the sample using a single optical element, for example, to study the shape and the existence or nonexistence of defects of a semiconductor or a similar object, a problem that arises is the reduction of the size of the primary beam (beam diameter) to scan the sample. Also in the multi-beam type charged particle beam apparatus, as in the single beam type electron beam inspection apparatus, when the aperture angle and the current density of the primary beam is increased to enhance the inspection speed, the aberrations of lenses and the beam blurring owing to the Coulomb repulsive force increase, resulting in reducing the inspection sensitivity. In addition, in the multi-beam type charged particle beam apparatus, the off-axis aberrations, which are caused when the primary beam runs along the trajectory that is away from the center of optical elements such as lenses, should be taken into account.

Another problem is to detect the secondary electron beams that are emitted from the sample by irradiating it with the plurality of beams. If it is possible to separate the secondary electron beams that are generated simultaneously at N portions on the sample by scanning N primary beams, to make them collide with the corresponding detectors, and to detect them individually, the signals can be acquired with high S/N ratios. On the contrary, if it is not possible to separate the secondary electron beams that are generated simultaneously at N portions on the sample, some parts of the secondary electron beams will collide with wrong detectors, which will worsen the S/N ratios. Therefore, it is necessary to control the secondary beam optical system so that the secondary beams emitted from plural portions on the sample are distributed separately with each other on the detectors.

These two problems and the relationship with the allocation of the primary beam will be explained in detail. From the viewpoint of the primary beam diameter, In order to decrease the off-axis aberrations, it is more advantageous to place the primary beam irradiated on the sample closer to the central axis. On the other hand, by placing the primary beam irradiated on the sample closer to the central axis, the primary beams get closer with each other, so the intervals among the positions of the secondary beam generation on the sample become narrower. Consequently, it becomes difficult to control the secondary beam optical system to distribute the secondary beam separately with each other on the detector, resulting in decreasing the degree of separability of the secondary beams (the fraction of the secondary beams that are detected by the specified detectors among all the secondary beams generated by the irradiation of the same primary beam). As mentioned above, two problems of decreasing the beam diameter of the primary beam and separately detecting the secondary beams are in the relationship of trade-off.

On the other hand, in the semiconductor process, the property of wafer is different for each product class, process, and lot; and the processing conditions for carrying out the high precision processing also vary for each case. For example, in the semiconductor inspection apparatus, the inspection specifications for obtaining a high sensitivity in detecting defects change by the property of the wafer sample. Here, the inspection specifications represent the inspection method or the inspection conditions that directly determine the effect of the inspection. For example, according to the material and thickness of the film to form a pattern, and the structure of the pattern, optimizing the measurement conditions such as the size of the primary beam (beam diameter) to scan the sample and the energy of the primary beam when it is entered on the sample are effective for obtaining a high sensitivity in detecting defects. In addition, the optimum inspection specifications depend on what kind of defect is to be detected. For example, to detect electrical defects, it is necessary to adjust the current density of the primary beam that enters in the sample and the electric field on the sample surface to make a desired charged state. Conversely, in detecting the pattern shape defects, the beam diameter influences the sensitivity in detecting the defects rather than the charged state of the sample surface.

The purpose of the present invention is to provide a charged particle beam apparatus that can process the sample with various properties as mentioned above at high precision and high speed.

In order to accomplish the above-mentioned purpose, for the first embodiment of the present invention, in the multi-beam type semiconductor inspection apparatus, the allocation of the primary beam on the sample is made changeable, and furthermore, the beam allocation for carrying out the inspection of the sample with the optimum inspection specification at high speed is selected. Also, the property of the selected primary beam is measured and adjusted. In addition, in another embodiment of the present invention, not only the beam allocation but also many optical parameters and instrument parameters are made changeable, and these are optimized.

According to an aspect of the present invention, a charged particle beam apparatus that can achieve both high defect-detection sensitivity and high inspection speed can be realized.

DETAILED DESCRIPTION OF THE PREFERRED EMBODIMENTS

Hereinafter, the present invention will be explained in detail by describing some preferred embodiments of the invention with reference to the accompanying drawings. In addition, for all the drawings to describe the embodiments of the invention, the same reference numerals are given for the same component to abbreviate the repeated explanations.

First Embodiment

Figure 1:
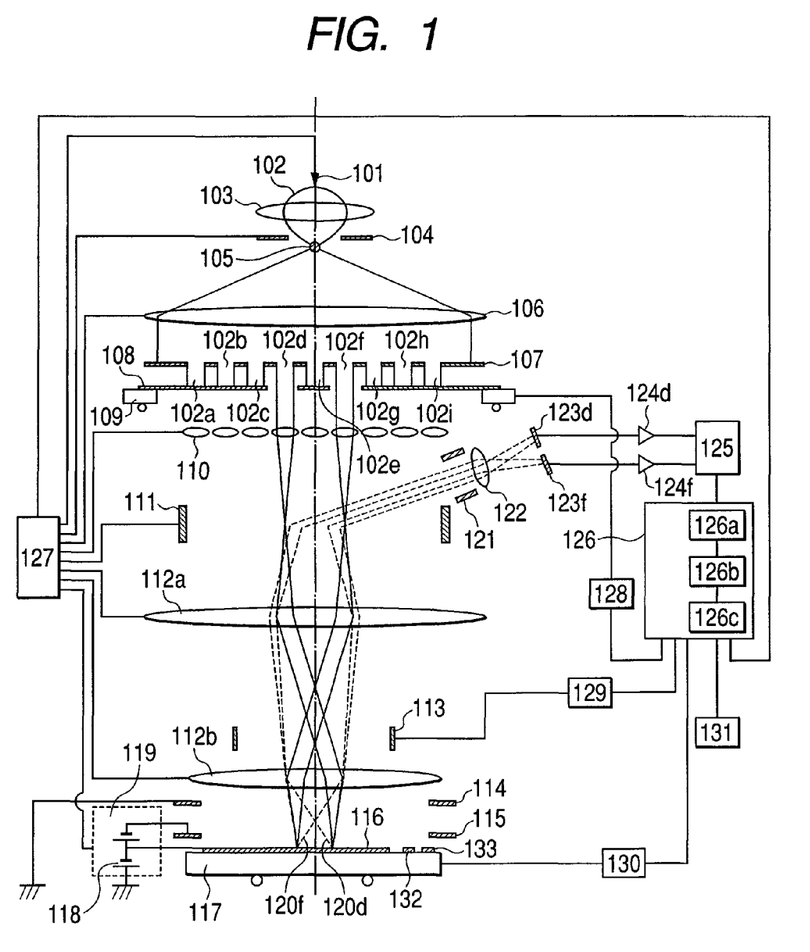
FIG. 1 is a diagram showing the general configuration of an electron beam inspection apparatus for explaining the first embodiment of the present invention.

FIG. 1 shows a skeleton framework of the multi-beam type semiconductor inspection apparatus related to the first embodiment of the present invention. The electron optical system of this apparatus is divided into a primary optical system controlling the primary beam that is emitted from a cathode 101 and reached to a sample 116, and a secondary optical system controlling the secondary beam that is generated by the interaction of the primary electron beam and the sample. The chain line represents an axis that should coincides with the symmetric axis of the roughly rotational-symmetrically formed optical system; in short, this axis is considered to be the mechanical central axis of the charged particle beam optical axis. This axis becomes a basis of the primary electron beam optical path. Hereinafter, this axis is referred to as central axis.

First, configuration of the apparatus is explained. A cathode 101 is made from a material with a low work function. For the cathode 101, by applying a high electric potential to an anode 104, an accelerating electric field is formed between the cathode 101 and the anode 104. An electromagnetic lens 103 superimposes a magnetic field on this accelerating electric field. In the downstream of the anode 104, a condenser lens 106, an aperture array 107 in which plural apertures is arranged on the same board, a beam selection aperture 108 and a beam selection stage 109 on which the beam selection aperture is mounted and moved, a lens array 110 with plural apertures, a Wien filter 111, objective lenses 112a and 112b, a deflector 113, a ground electrode 114, and a surface electric field control electrode 115 are allocated, composing the primary optical system. As is not shown in the figure, in the primary optical system, a current limiting aperture, an aligner for adjusting the central axis (optical axis) of the primary beam, and other devices are allocated.

The stage 117 moves with a wafer 116 mounted on it. A negative electric potential (hereinafter, referred to as retarding electric potential) is applied to the wafer 116. As is not shown in the figure, a wafer holder exists between the wafer 116 and the stage 117 in the electrically conducted state with the wafer; and by connecting a retarding power supply 118 to this wafer holder, a desired voltage is applied to the wafer holder and the wafer 116. On the stage 117, a reference sample 132 that is used for adjusting the electron optical conditions and measuring the adjusted state, and a Faraday cup 133 that is used for measuring the electron beam current are provided. As is not shown in the figure, the system control section 126 is connected to the Faraday cup 133 through an amplifier.

The surface electric field control electrode 115, the ground electrode 114, the objective lenses 112a and 112b, and the Wien filter 111 are also the parts of the secondary optical system. In the secondary optical system, a secondary beam axis adjustment aligner 121, a secondary beam condenser lens 122, and other devices are also allocated, playing a role to make the secondary beam enter in detectors 123d and 123f.

The system control section 126 is connected to the detectors 123d and 123f, and amplifier circuits 124d and 124f through an A/D converter 125, composing a signal detection system. In addition, two sets of detectors and amplifier circuits are shown in FIG. 1; however, in the actual embodiment, plural the sets of detectors and amplifier circuits are provided according to the number of primary beams that can be formed.

The system control section 126 is a part of the control system that controls the whole apparatus systematically. The control system consists of the system control section 126, an optical system control circuit 127, a selection stage control circuit 128, a scan signal generation circuit 129, a stage control circuit 130, and other control devices. The cathode 101, the anode 104, the condenser lens 106, the aperture array 107, the Wien filter 111, the objective lenses 112a and 112b, the retarding power supply 118, and a surface electric field control power supply 119 are connected to the system control section 126. In addition, as is not shown in the figure, the secondary beam axis adjustment aligner 121 and the secondary beam condenser lens 122 are also connected to the system control section 126 through the optical system control circuit 127. The beam selection stage 109 is connected to the system control section 126 through the selection stage control circuit 128. The deflector 113 is connected to the system control section 126 through the scan signal generation circuit 129. The stage 117 is connected to the system control section 126 through the stage control circuit 130. An image display unit 131 is connected to the system control section 126.

The signal detection system is also controlled by the system control section. The timing of the signal detection for the detectors 123d and 123f is determined by a clock signal that the system control section 126 generates. That is, the signals of the secondary beam are acquired synchronous with the clock signals, and the signal of the secondary beam acquired within one clock interval becomes the brightness signal of the one pixel of an image that is formed by the detected signals.

On the other hand, a length that the deflector 113 scans the primary beam on the sample within one clock interval corresponds to the width of one pixel of the image that is formed by the detected signals.

In addition, as is not shown in the figure, compositional units other than the signal detection system, the system control section 126, and each control circuit are allocated in vacuum chambers, and they are, needless to say, operated after they are evacuated. In addition, a wafer transfer system, which allocates a wafer on the stage from the outside of vacuum, is, needless to say, provided.

Figure 2A:
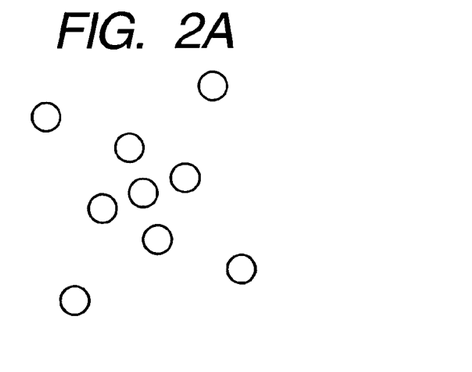
FIG. 2A is a diagram explaining the allocation of openings of the aperture lens array.

Next, operations and details of the apparatus will be explained. The primary beam 102 emitted from the cathode 101 is accelerated in the direction of the anode 104 while receiving a focusing action by the electromagnetic lens 103, forming a cathode image 105 (a point at which the beam diameter becomes minimum). As is not shown in the figure, an extraction electrode is provided between the cathode 101 and anode 104, as is often seen in a commonly-used electron gun. Also, in the vicinity of the anode 104, an aperture is allocated. By changing the operation conditions of the cathode 101, the extraction electrode, the electromagnetic lens 103, and the anode 104, it is possible to adjust the current of the primary beam passing through the aperture and the size of the cathode image 105. In addition, as is not shown in the figure, in the downstream side of the anode 104, an aligner to correct the axis of the primary electron beam is allocated, realizing a structure to enable to correct the axis of the primary beam when it is shifted for the electron optical system in the downstream side. The condenser lens 106 aligns the primary beam, whose light source is the cathode image 105, parallel. The aperture array 107 arranges plural apertures on the same board, and has 9 apertures in the present embodiment. By unit of the aperture array 107, the primary beam 102 is divided into 9 primary beams: 102a, 102b, 102c, 102d, 102e, 102f, 102g, 102h, and 102j used for inspection. In addition, in FIG. 1, the 9 primary beams are drawn as if they are arranged linearly; but actually, they are arranged two dimensionally in a plane perpendicular to the central axis as shown in FIG. 2A. Furthermore, the allocation of each primary beam shown in FIG. 2B to FIG. 2E is rotationally symmetric, and the center of the rotational symmetry coincides with the central axis in FIG. 1.

Figure 2B:
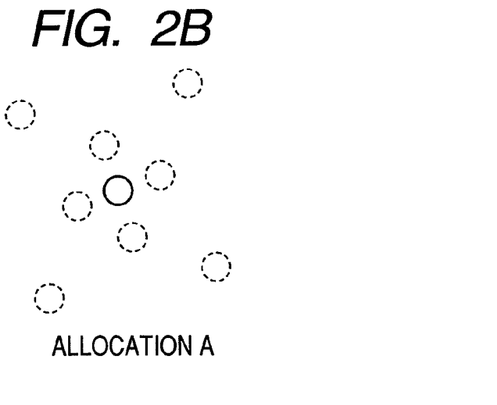
FIG. 2B is a diagram explaining the beam allocation A.
Figure 2C:
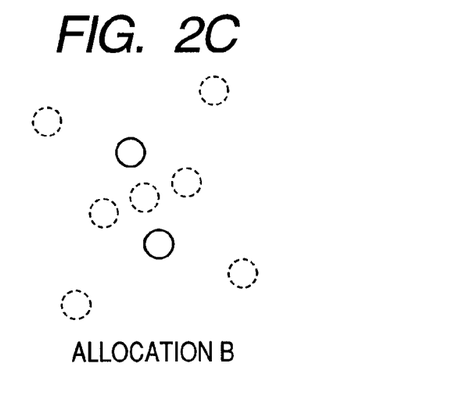
FIG. 2C is a diagram explaining the beam allocation B.
Figure 2D:
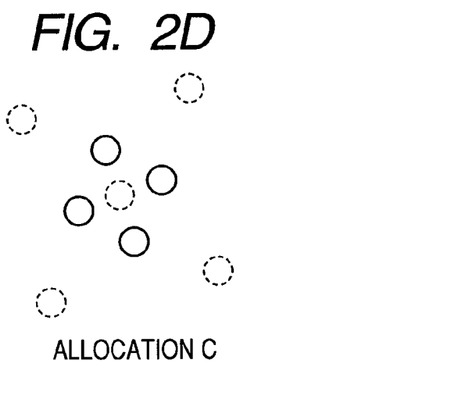
FIG. 2D is a diagram explaining the beam allocation C.
Figure 2E:
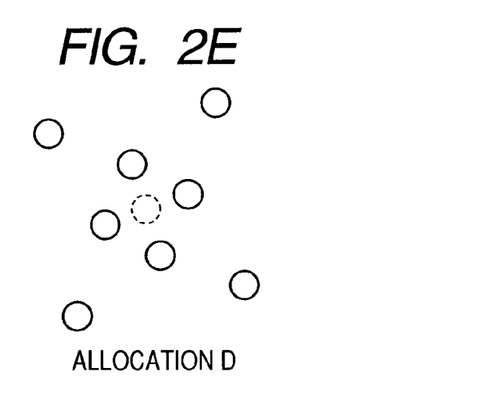
FIG. 2E is a diagram explaining the beam allocation D.

The beam selection aperture 108 is a board having plural apertures, and it is mounted on the beam selection stage 109. When the selection stage control circuit 128 is moved by the control of the system control section 126, the relative positional relationships between the openings of the beam selection aperture 108 and the 9 primary beams: 102a, 102b, 102c, 102d, 102e, 102f, 102g, 102h, and 102j are adjusted. That is, the position of the beam selection stage 109 is controlled so that only a desired beam among the 9 primary beams passes through the opening of the beam selection aperture 108, and enters in the optical system in the downstream side. In the present embodiment, the shape of the openings of the beam selection aperture 108 and the beam selection stage is designed so that four different ways of beam allocations from an allocation A as shown in FIG. 2B to an allocation D as shown in FIG. 2E become the candidates. Therefore, one, two, four, or eight primary beams can enter in the optical system in the downstream side. In FIG. 1, two primary beams 102d and 102f are selected, and enter in the optical system in the downstream side.

Here, the relationship between the allocation of each beam and the beam diameter of the primary beam will be explained. The allocation of the primary beam corresponding to the allocation A is the same as the single beam; the primary beam is formed on the central axis, and no off-axis aberration is generated. In addition, because the beam current irradiated on the sample is low, the beam blurring owing to the Coulomb repulsive force is small. Therefore, among the allocations from A to D, the beam diameter of the primary beam on the sample is smallest in the allocation A. On the other hand, in the allocation B, because the primary beam is formed away from the central axis, the off-axis aberrations are generated, and the total current of the primary beam becomes double; so the beam blurring owing to the Coulomb repulsive force becomes larger than that of the allocation A. Therefore, the beam diameter of the primary beam on the sample is larger than that of the allocation A. In the allocation C, the distance between the primary beam and the central axis is equal to that of the allocation B, the off-axis aberrations are equal to that of the allocation B; however, because the beam blurring owing to the Coulomb repulsive force becomes larger than that of the allocation B, the beam diameter of the primary beam on the sample becomes larger than that of the allocation B. Furthermore, in the allocation D, the distance between the primary beam and the central axis becomes larger than that of the allocation B and the allocation C, the off-axis aberrations become larger, and moreover, the beam blurring owing to the Coulomb repulsive force becomes larger than that of the allocation C. Therefore, the beam diameter of the primary beam on the sample becomes largest among the allocations from A to D. On the other hand, inspection speed is lowest in the allocation A in which the number of beams is smallest, and the inspection speed becomes higher in the order of the allocations B, C, D. In addition, the inspection speed can be expressed by the area of region in which plural primary beams scan in unit time. The measurement speed can be expressed with nearly the same definition.

By returning to FIG. 1 again, operations and details of the apparatus will be explained.

The selected primary beams 102d and 102f are focused individually by the lens array 110. The lens array 110 consists of three sheets of electrodes each of which has plural openings; by applying a voltage to the middle electrode among the three electrodes, this lens array acts as an einzel lens for the primary beams passing through the openings.

The two primary beams 102d and 102f focused individually by the lens array 110 pass through inside the Wien filter 111. The Wien filter 111 generates a magnetic field and an electric field, which are at right angles to each other, in a plane roughly perpendicular to the incident direction of the primary beam, and gives a deflection angle for the passing electron corresponding to the energy. In the present embodiment, the electric field strength and magnetic field strength are set so that the primary beam goes straight, and furthermore, for the secondary beam that enters from the opposite direction, the electric field strength and magnetic field strength are adjusted and controlled so that the secondary beam deflects to a desired angle. In addition, for the position of the Wien filter 111, by taking the effect of aberrations for the primary beam into account, to reduce the effect, it is allocated to match the height of the primary beam that is focused by the lens array 110. Components 112a and 112b are one set of objective lenses, and both are electromagnetic lenses. They project the primary beam focused by the lens array 110 on the sample 116 at a reduced magnification.

The deflector 113 for the scan deflection is made of an electrostatic octapole, and installed in the objective lens. By the control of the system control section 126, the scan signal generation circuit 129 generates a signal at a predetermined amplitude and frequency. When this signal enters in the deflector 113, the primary beam passing through inside the deflector receives a deflecting action in nearly the same direction and by nearly the same angle to carry out the raster scanning on the sample, namely, the wafer 116. To the wafer 116, a negative electric potential is applied from the retarding power supply 118. Therefore, between this wafer and the ground electrode 114 that is connected to the ground electric potential, an electric field to deaccelerate the primary beam is formed. The unit 115 is the surface electric field control electrode, and it is a disk like electrode having a circular opening. The diameter of the opening of the surface electric field control electrode 115, the distance between the surface electric field control electrode 115 and the sample 116, and the output voltage of the surface electric field control power supply 119 connected to the surface electric field control electrode 115 determine the electric field intensity on the surface of the sample 116.

The surface electric field control power supply 119 is a power supply connected to the surface electric field control electrode 115. The retarding power supply 118 and the surface electric field control power supply 119 are systematically controlled by the system control section 126 through the optical system control circuit 127 as well as other optical elements, more specifically, the cathode 101, the anode 104, the condenser lens 106, the lens array 110, the Wien filter 111, and the objective lenses 112a and 112b.

The stage 117 is controlled by the stage control circuit 130. The system control section 126 controls the scan signal generation circuit 129 and the stage control circuit 130 systematically to inspect a predetermined region on the wafer 116 one stripe by one stripe that are aligned in the stage driving direction. In addition, in the inspection apparatus of the present embodiment, the apparatus is controlled so that the primary beam scans the belt-like regions sequentially by combining the deflection scan and the stage movement while the stage is moving continuously.

By irradiating the primary beam on the sample, secondary beams such as secondary electron beam and backscattered electron beam are generated from the sample 117. In FIG. 1, the two primary beams 102d and 102f are irradiated on the sample; so the secondary beams 120d and 120f are generated from the two positions on the sample where these primary beams are irradiated, respectively. The secondary beams 102d and 102f receive the focusing actions of the objective lenses 112a and 112b, and by the Wien filter 111 that has a deflecting action for the secondary beams, the trajectories of the secondary beams are separated from the trajectories of the primary beams. After that, the trajectories of the secondary beams are corrected by the secondary beam axis adjustment aligner 121, and furthermore, by the focusing action of the secondary beam condenser lens 122, the secondary beams reach the detectors 123d and 123f, respectively. Signals detected by the detectors 123d and 123f are amplified by the amplifier circuits 124d and 124f, digitized by the A/D converter 125, and stored once in a memory device 126a in the system control section 126 as an image data. After that, an arithmetic section 126b calculates various statistics values of the image, and finally, a defect judgment section 126c judges the existence or nonexistence of defects based on the predetermined defect judgment conditions. The judged results are displayed on the image display unit 131. In addition, when an electron beam apparatus of the present embodiment is used for a length measurement SEM, a length measurement execution section that carries out the length measurement based on the image pixel data (two-dimensional intensity distribution data of secondary electrons or backscattered electrons) stored once in the memory device 126a is provided instead of the defect judgment section 126c.

Figure 3:
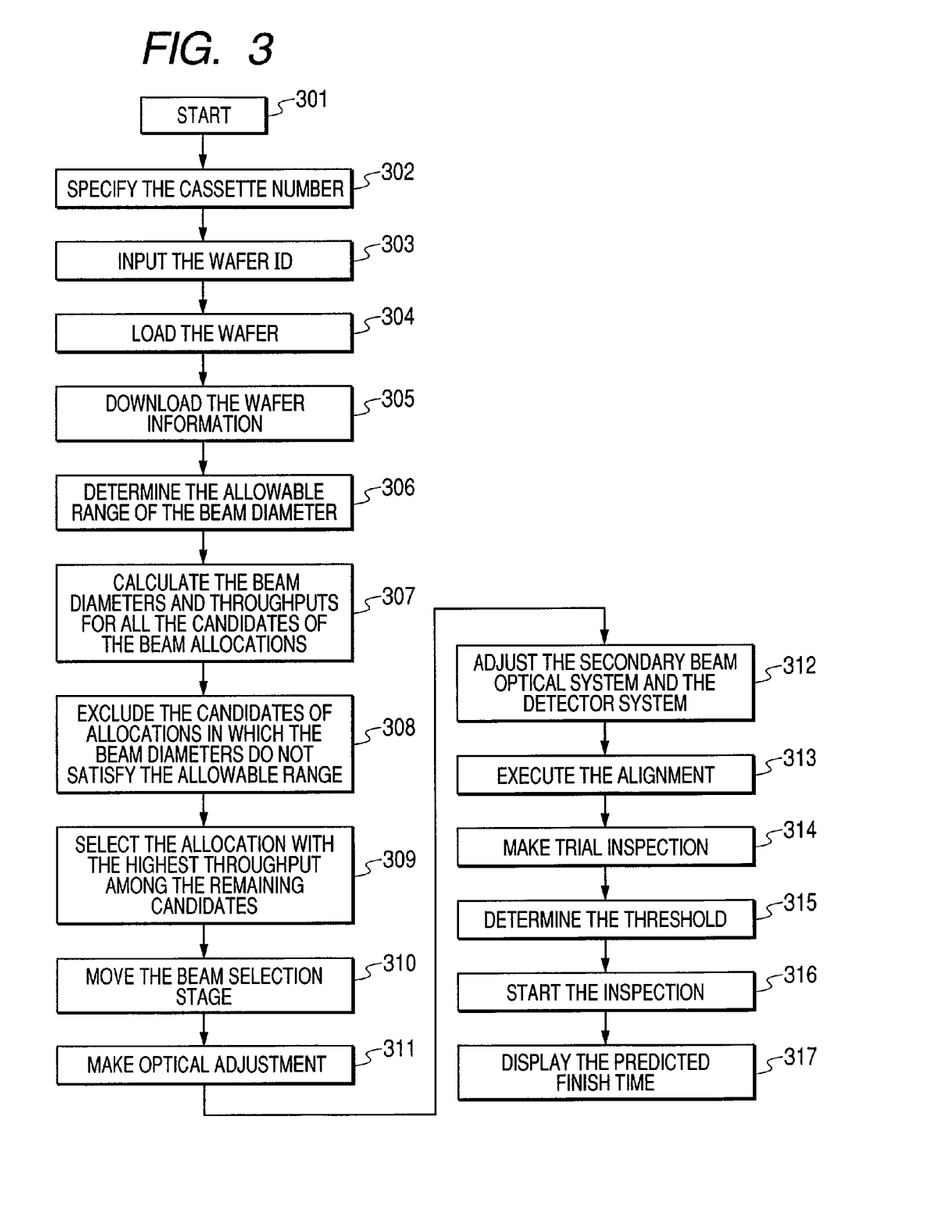
FIG. 3 is a flowchart explaining the first embodiment of the present invention.

Next, the procedure for carrying out the inspection in the present embodiment will be explained in detail with reference to the flowchart shown in FIG. 3.

When an operator click the Start button displayed on the image display unit 131 (step 301), the input window is displayed to specify a cassette (not shown in the figure) in which a wafer to inspect is stored. When the operator input the cassette number (step 302), the wafer ID input window is displayed. The operator inputs the lot ID and the wafer ID to which the wafer to inspect belongs (step 303). Based on these IDs, the system control section 126 judges the wafer size and other information about the wafer, and mounts the wafer on the stage 117 using the wafer loader (not shown in the figure) (step 304).

In step 305, the system control section 126 downloads the information of the wafer to inspect such as the product class, the process, the material and the thickness of the film to form on the pattern, the pattern shape, and the pattern size (design size) from the server for factory administration based on the wafer ID. Here, the process represents the information on how far the wafer to inspect (or to measure) has gone through the manufacturing process of a structural object (for example, a semiconductor device or a magnetic head) that is formed on the wafer, and more specifically, it corresponds to the information on how far the layer on the wafer has been formed. In addition, the pattern represents a pattern (such as wiring or contact hole) of the structural object formed on the wafer. Or, the operator may input this information through the wafer information input window displayed on the image display unit 131.

In step 306, the system control section 126 determines the allowable range of the beam diameter of the primary beam to scan the sample based on the information that the system control section 126 has downloaded in step 305.

In step 307, the system control section 126 calculates the beam diameter and current of the primary beam on the sample using a formula memorized beforehand for all the candidates of the beam allocations. Furthermore, based on the calculated result of the current, the inspection speed is estimated as shown in the table below:

| Allocation | Number of beams | Primary beam diameter | Current | Inspection speed |
|---|---|---|---|---|
| A | 1 | 30 nm | 50 nA | 25 cm²/h |
| B | 2 | 40 nm | 100 nA | 50 cm²/h |
| C | 4 | 50 nm | 200 nA | 100 cm²/h |
| D | 8 | 60 nm | 400 nA | 200 cm²/n |

In step 308, the system control section 126 refers to the allowable range that is determined in step 306, and excludes the candidates of the beam allocations in which the beam diameter does not satisfy the allowable range. For example, when the pattern size formed on the sample, that is, wafer is large, and if the allowable range of the primary beam diameter is less than or equal to 60 nm (case I), any beam allocation from the allocation A to the allocation D satisfies the allowable range. However, when the pattern size formed on the wafer is small, and if the allowable range of the primary beam diameter is 40 nm or equal to 40 nm (case II), the allocation A and the allocation B satisfy the allowable range, but the allocation C and the allocation D do not satisfy the allowable range, so they are excluded from the candidates.

In step 309, the system control section 126 selects the beam allocation that attains highest inspection speed from the candidates that have not been excluded in step 308. For example, in case I in which the candidates of allocations from the allocation A to the allocation D remain, the allocation D with the highest inspection speed among them is selected. In case II in which only the candidates of allocations of the allocation A and the allocation B remain, the allocation B with the higher inspection speed between two allocations is selected. The selected beam allocations are stored in the system control section 126 as log data. Also, they may be displayed on the image display unit 131.

In step 310, in order to actualize the beam allocation selected in step 309, the system control section 126 moves the beam selection stage through the selection stage control circuit 128. More specifically, by adjusting the relative positional relationship between the primary beams formed by the aperture array and the openings of the beam selection aperture 108, the openings of the beam selection aperture 108 mounted on the beam selection stage 109 allow only the predetermined beams to enter the optical system in the downstream side, and blocks off the remaining beams.

In step 311, optical adjustment is performed for the primary beams that enter in the optical system in the downstream side in step 310. By using the reference sample 132, the Faraday cup 133, and other devices that are mounted on the stage 117, the property of the primary beam such as beam diameter and current are measured for each one of the N primary beams selected in step 310, and whether or not the beam diameter falls within the allowable range is confirmed. If the primary beam is estimated to be shifted for the electron optical system, the shift is corrected using the aligner (not shown in the figure). After correcting the shift, the property of the primary beam such as the beam diameter and current are measured again, and the measurement result is displayed on the image display unit 131 for each one of the N primary beams. In addition, every optical parameter such as the voltage applied to the aligner, and the measurement results of the beam diameter and current are stored in the system control section 126 as the log data.

In step 312, the system control section 126 irradiates the primary beams, which are entered in the optical system in the downstream side in step 310, through the optical system control circuit 127 on the sample 116 or the reference sample 132, separates the generated secondary beams, and adjusts the voltage (or current) applied to the secondary beam axis adjustment aligner 121, and adjusts the focal length and other parameters of the secondary beam condenser lens 122 so that the secondary beams enter in the respective predetermined detectors. Furthermore, the system control section 126 adjusts the gain, offset, and other parameters of the amplifier circuits 124*d* and 124*f*, and fixes up the waveform of the signals input in the A/D converter 125.

In step 313, the specification window for the alignment is displayed on the image display unit 131, and when the operator specifies plural points in an alignment chip on the wafer through this window, the apparatus detects the alignment mark automatically, and corrects the stage coordinates for the wafer; that is, the alignment is executed.

Figure 4A:
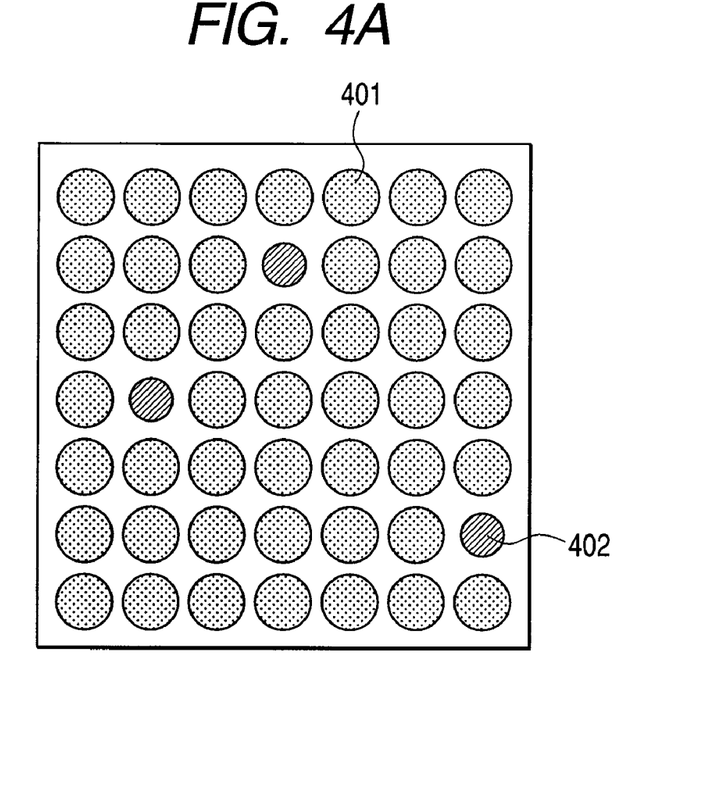
FIG. 4A shows an example of an image obtained by a trial inspection.
Figure 4B:
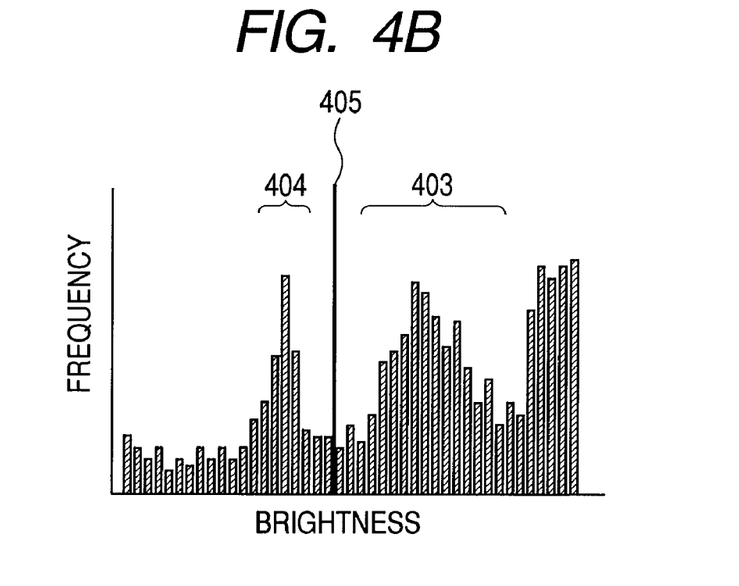
FIG. 4B is a histogram display of the image brightness.

In step 314, a trial inspection is performed. Under the optical conditions for which the apparatus has been adjusted up to the step 313, a trial inspection is carried out for a small region within a predetermined chip. FIG. 4A is an example of a pattern image within the trial inspection region. Among the patterns arranged like a matrix, the brightness is different between a normally formed pattern 401 and a poorly formed pattern 402. FIG. 4B shows the histogram display for the brightness of every pixel in this image. 403 represents a peak corresponding to the normally formed pattern; and 404 represents a peak corresponding to the poorly formed pattern.

In step 315, the operator sets a threshold value of the image contrast to use it for judging defects. In the example of FIG. 4A and FIG. 4B, by setting a threshold value 405 between the peak 403 corresponding to the normally formed pattern and the peak 404 corresponding to the poorly formed pattern, it is expected that the defects can be detected with a high sensitivity.

After setting the optimum threshold value, the operator clicks the Inspect button displayed on the image display unit 131 to start the actual inspection (step 316). The system control section 126 memorizes the time when the inspection is started, predicts the inspection finish time based on the inspection speed that is calculated in step 307, and displays the inspection finish time on the image display unit 131.

In addition, in the present embodiment, in step 306, the system control section 126 determined the allowance range of the beam diameter of the primary beam to scan the sample; however, when the sample is a product class with no inspection record such as when the pattern formed on the wafer is newly designed and when a new process is applied to form the pattern, the system control section 126 will not be able to automatically determine the allowance range of the beam diameter of the primary beam. In such a case, the operator may input the allowance range of the beam diameter of the primary beam to scan the sample through the inspection specification input window displayed on the image display unit 131.

Furthermore, in the present embodiment, in step 307, the system control section 126 calculated the beam diameter and current of the primary beam on the sample by letting the beam allocation as a variable parameter; however, if an aperture array having different sizes of openings is mounted on the movable stage, the aperture half-angle of the beam that is cut out by the aperture can be variable.

In such a case, the system control section 126 is well to calculate the primary beam diameter, current, and the inspection speed for all the combinations of the beam allocations and the beam aperture half-angles in step 307. For example, if there are four ways in the beam allocations, and three ways of the beam aperture half-angles can be taken, there are 12 ways of combinations; so, the primary beam diameter, current, and the inspection speed are calculated for every combination. Or, it is well to obtain the information by referring to the data measured beforehand. In step 308, from the 12 ways of combinations, the candidates of the beam allocations, which do not satisfy the allowable range of the beam diameter, are excluded from the candidates, and in step 309, it is well to select the combination of the highest inspection speed.

Furthermore, in the present embodiment, by using the beam selection aperture 108 and a beam selection stage 109 on which the beam selection aperture is mounted, only the predetermined beams were entered in the optical system in the downstream side, and remaining beams were blocked off. Or, by using blanking electrodes that act individually on plural the charged particle beams, it is also possible to achieve a similar advantageous effect as the present embodiment.

In addition, in the present embodiment, the advantageous effect of the present invention was explained by taking an electron beam inspection apparatus as an example; however, the similar advantageous effect of the present invention can also be obtained in various apparatuses such as a length measurement SEM that measures the size of a pattern formed on the sample, an inspection apparatus that checks the existence or nonexistence of defects of a pattern formed on the sample, and a review SEM that observes a defect of a pattern formed on the sample. The similar advantageous effect can also be obtained when a SIM observation is performed by transforming an ion beam generated at an ion source into multiple beams and irradiating them on the sample.

Second Embodiment

In the first embodiment, in order to take a balance between the two problems of decreasing the beam diameter of the primary beam and separately detecting the secondary beams, which are in the relationship of trade-off, among the candidates of the beam allocations that satisfy the allowable range of the primary beam, the beam allocation with the highest inspection speed was selected. In the present embodiment, by extending the first embodiment, not only the allocations of the primary beam, but also many parameters are made variable. With this, after setting the optimum specifications for the sample, the conditions capable of performing the inspection at the highest speed are searched.

Hereinafter, the present embodiment will be explained in detail with reference to FIG. 1.

As mentioned in the summary of invention, in the semiconductor inspection apparatus, the optimum inspection specifications change according to the product class and the process of the sample, namely, wafer. Here, the specifications are determined by the resolution of an image formed by detected signals, the energy and current density of the primary beam when it enters on the sample, and the specification parameter such as the electric field intensity on the sample surface. Hereinafter, these parameters, which directly determine the advantageous effect, are referred to as specification parameters.

These specification parameters have the following relationship with the control system parameters such as the accelerating voltage (an electric potential difference between the cathode 101 and the anode 104), the retarding voltage applied to the sample 116, a voltage applied to the surface electric field control electrode 115, the focal lengths of the various lenses (the electromagnetic lens 103, the collimator lens 106, the lens array 110, the objective lenses 112a and 112b), the optical system parameters such as the scan width of the primary beam on the sample 116, the frequency of the clock signals that the system control section 126 generates, the pixel size of the image formed by the detected signals, and the stage moving speed.

The resolution of the image formed by the detected signals is determined by the beam diameter of the primary beam to scan on the sample, the pixel size of the image that is formed based on the signals of the detected secondary beam, and the S/N ratio of the detected signals.

The beam diameter of the primary beam is determined not only by the size of the cathode image 105, which is determined by the operation conditions of the electron gun constructed from the anode 104 and the electromagnetic lens 103, but also by the focal lengths and the retarding voltages of the various lenses (the electromagnetic lens 103, the collimator lens 106, the lens array 110, the objective lenses 112a and 112b), and the optical magnification that is determined by the voltage applied to the surface electric field control electrode 115, and furthermore by the aberrations generated in each optical element and the amount of the beam blurring owing to the Coulomb repulsive force. Therefore, the beam diameter of the primary beam is also related with other conditions such as the distance of the primary beam from the central axis, the scan width of the primary beam on the sample 116, and the current and the aperture angle of the primary beam.

The pixel size is the value of the scan width of the primary beam on the sample 116 divided by the number of pixels per one scan. The S/N ratio is determined by the energy of the incident primary beam on the sample and the kind of the film composing the sample surface, which determine the yield (the ratio of the amount of the generated secondary beam to the amount of the incident primary beam), the current density and the pixel size of the primary beam, the scan speed, the degree of separability of the secondary beams, and other conditions.

The energy of the incident primary beam on the sample is determined by the accelerating voltage (the electric potential difference between the cathode 101 and the anode 104) and the retarding voltage applied to the sample 116.

The current density of the primary beam is determined by the beam diameter of the primary beam as mentioned above and the current of the primary beam.

The electric field intensity on the sample surface is determined by the positions and shapes of the ground electrode 114 and the surface electric field control electrode 115, the retarding voltage applied to the sample 116, and the voltage applied to the surface electric field control electrode 115.

On the other hand, the inspection speed is determined by the stage moving speed and the pixel size. The stage moving speed is determined by the scan width, scan speed, and the settling time of the deflection signal that is given from the scan signal generation circuit 129 to the deflector 113.

As mentioned above, the specification parameters and the inspection speed are determined by the many optical system parameters, the control system parameters and the allocation of the beams. Therefore, in order to optimize the specification parameters according to the sample, it is necessary to adjust the combination of the above-mentioned optical parameters and the control system parameters; however, in some samples, when the optical parameters and the control system parameters are adjusted, the electromagnetic field distribution along the passage of the secondary beam changes, so the distribution of the secondary beams on the detector might change, resulting in decreasing the degree of separability of the secondary beams. In other words, the fraction of the secondary beams that do not enter the predetermined detector but enter other detectors or do not enter any detector might increase.

The relationship of the degree of separability of the secondary beams, optical parameter, and the allocation of the beams will be explained in detail by taking the inspection of electrical defects as an example. Because the electrical defects such as a contact failure, a wiring short-circuit, and a void can not seen on the surface, in order to detect these defects, an inspection method to charge up the film on the sample surface by irradiating electrons and to obtain the contrast of the image is effective. As mentioned above, the method to charge up the sample before the inspection or measurement is referred to as precharging. In order to enhance the advantageous effect of this precharging, during the inspection, when the primary beam scans on the sample, it is effective to sufficiently decrease the electric field intensity on the sample surface, and to increase the holding time of the charge accumulated by the precharging. However, because the electric field on the sample surface has an action to align the traveling directions of the secondary beams, decreasing the electric field intensity on the sample surface adversely affects the performance of the inspection from the standpoint of the separation detection of the secondary beams, so even if the secondary beam axis adjustment aligner 121 and the secondary beam condenser lens 122 are adjusted, the degree of separability of the secondary beams might decrease. Therefore, even when 9 primary beams can be formed by 9 openings as shown in FIG. 2A, if the primary beams on the sample take the allocation C or D as shown in FIG. 2D or FIG. 2E, the degree of separability of the secondary beams becomes low, and in some cases, the apparatus might not be able to detect the secondary beams with a sufficient S/N ratio. In such cases, to separate the secondary beams sufficiently, it might become advantageous to reduce the number of the primary beams and to broaden the interval of the primary beams on the sample. That is, the allocation B might become more advantageous. And, during the inspection, when it is necessary to reduce the electric field intensity on the sample surface furthermore, it might become more advantageous to reduce the number of the primary beams to one as in the allocation A.

Furthermore, in another example, when the film to form a pattern on the wafer is thin or other similar occasions, in order to increase the fraction of the primary beams to stop within the film, in some cases, it might be more effective to sufficiently decrease the energy of the primary beam to irradiate the sample for enhancing the sensitivity in detecting defects. However, if the energy of the primary beam is decreased, the beam diameter of the primary beam might become large owing to the chromatic aberration and the Coulomb repulsive force. In addition, in order to decrease the energy of the primary beam, when the retarding voltage applied to the sample 116 is adjusted, and furthermore, the focal length of each lens is adjusted according to this adjustment, the electromagnetic field distribution along the passage of the secondary beam might change. If this change is large, even the adjustments of the secondary beam axis adjustment aligner 121 and the secondary beam condenser lens 122 might not be able to fully correct the trajectory of the secondary beam, resulting in decreasing the degree of separability of the secondary beams. Therefore, as in the example of the inspection of electrical defects, in some cases, it might become necessary to reduce the number of the primary beams and to broaden the interval of the primary beams on the sample.

As another method to prevent the secondary beams from decreasing the degree of separability is to provide apertures to limit the intake angles of the secondary beams in the optical system of the secondary beams, that is, at any positions from the Wien filter 111 to the detectors 123d and 123f, and to prevent the secondary beams from being detected other than the predetermined detectors. However, this method not only decreases the noise of the detected signals, but also decreases the amount of signals themselves, so this method is not necessarily effective.

Consequently, in the present embodiment, the combination of the optical parameters, the control system parameters, and the beam allocations are optimized so that the apparatus can achieve a good balance between the optimum specifications for the inspection of the sample and the degree of separability of the secondary beams to obtain the sufficient S/N ratio, and furthermore can carry out the inspection at high speed.

Figure 5:
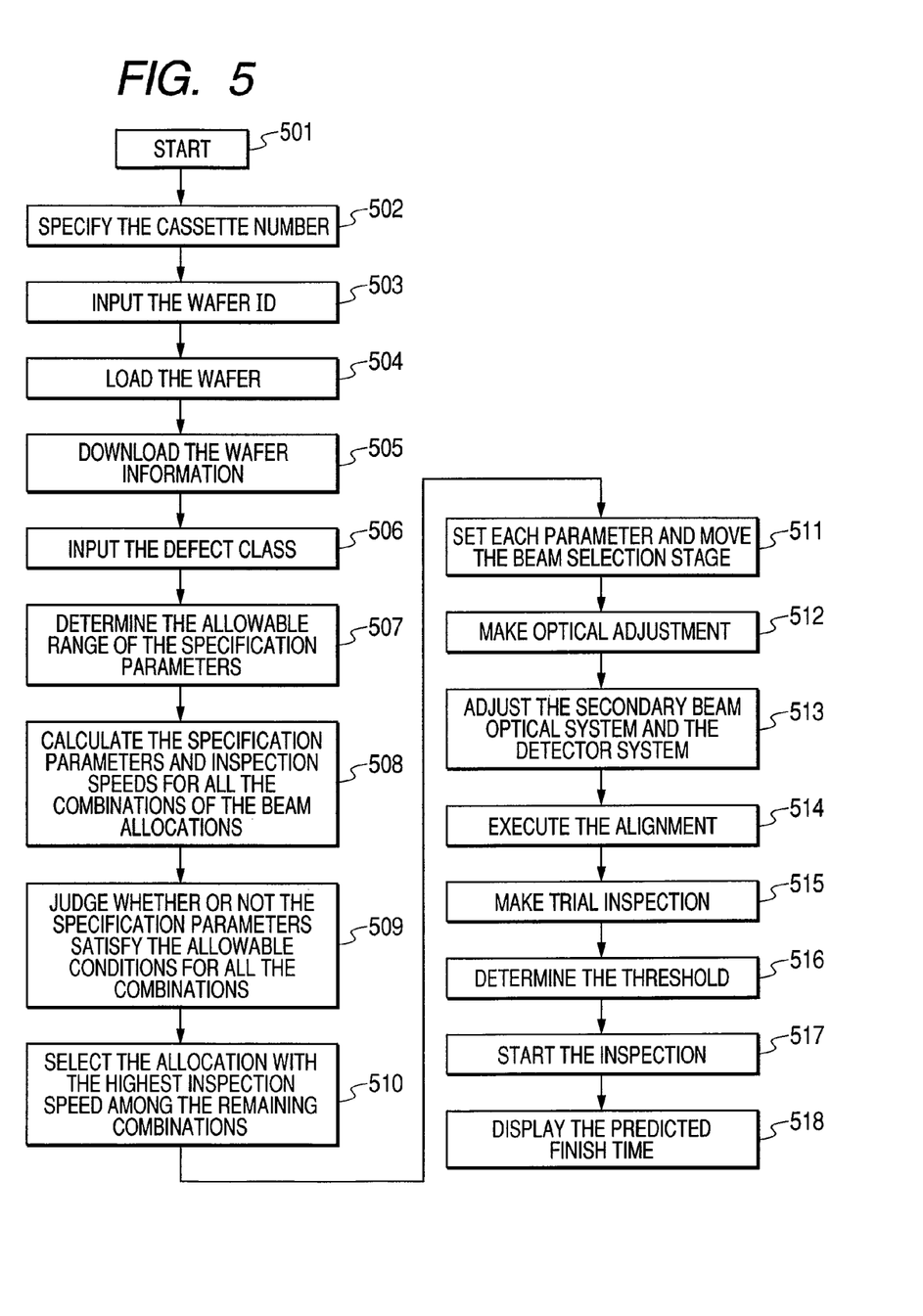
FIG. 5 is a flowchart explaining the second embodiment of the present invention.

The procedure for carrying out the inspection in the present embodiment will be explained in detail with reference to the flowchart shown in FIG. 5. When the operator click the Start button displayed on the image display unit 131 (step 501), the input window is displayed to specify a cassette (not shown in the figure) in which a wafer to inspect is stored. When the operator input the cassette number (step 502), the wafer ID input window is displayed. The operator inputs the lot ID and the wafer ID to which the wafer to inspect belongs (step 503). Based on these IDs, the system control section 126 judges the wafer size and other information about the wafer, and mounts the wafer on the stage 117 using the wafer loader (not shown in the figure) (step 504).

In step 505, the system control section 126 downloads the information of the wafer to inspect such as the product class, the process, the material and the thickness of the film to form on the pattern, the pattern shape, and the pattern size (design size) from the server for factory administration based on the wafer ID. Or, the operator may input this information through the wafer information input window displayed on the image display unit 131.

In step 506, the operator specifies the defect class through the Defect class specification window displayed on the image display unit 131. Or, the system control section 126 may automatically select the defect class based on the wafer information obtained in step 505. Here, specifying the defect class represents selecting whether the defect to detect is an electrical defect (such as a contact failure, a wiring short-circuit, and avoid), a shape defect (such as a crack and a protrusion in defective bore), or a foreign substance.

In step 507, the system control section 126 determines the allowable range of the specification parameters based on the wafer information obtained in step 505 and the defect class selected in step 505. Here, the specification parameters directly determine the advantageous effect of the inspection, and in this embodiment, they represent the resolution of the image formed by the detected signals, the energy and the current density of the incident primary beam on the sample, and the electric field intensity on the sample surface.

In step 508, the system control section 126 calculates the value of every specification parameter and the estimated inspection speed for all the combinations of the optical parameters, the control parameters, and the beam allocations referring to a formula that has been memorized beforehand in the memory area inside the system control section, or referring to a table that has been memorized beforehand in the memory area inside the system control section. On this occasion, the degree of separability of the secondary electron beams is calculated based on the beam allocation, and based on the calculated result, the resolution is calculated. The value of every specification parameter and the predicted value of the inspection speed that are obtained from the calculation are stored in the memory area inside the system control section 126.

In step 509, the system control section 126 judges whether or not the each specification parameter calculated in step 508 satisfies the allowable conditions that were determined in step 507 for all the combinations of the optical parameters, the control parameters, and the beam allocations, and excludes the combinations that do not satisfy the allowable range.

In step 510, the system control section 126 selects the combination with the highest inspection speed among the combinations that were not excluded in step 509. With this, the combination of the optical parameters, the control parameters, and the beam allocation is determined. The selected parameters and the beam allocation are stored in the system control section 126 as the log data. In addition they may be displayed on the image display unit 131.

In step 511, in order to actualize the combination of the optical parameters and the control parameters, the system control section 126 inputs the optical parameters and the control parameters that are selected in step 509 to the optical system control circuit 127, the stage control circuit 130, the arithmetic section 126b of the system control section 126, and the scan signal generation circuit 129. Also, the system control section 126 inputs the beam allocation selected in step 509 to the selection stage control circuit 128. With this, only the predetermined beams among the primary beams formed by the aperture array enter the optical system in the downstream side.

Figure 6:
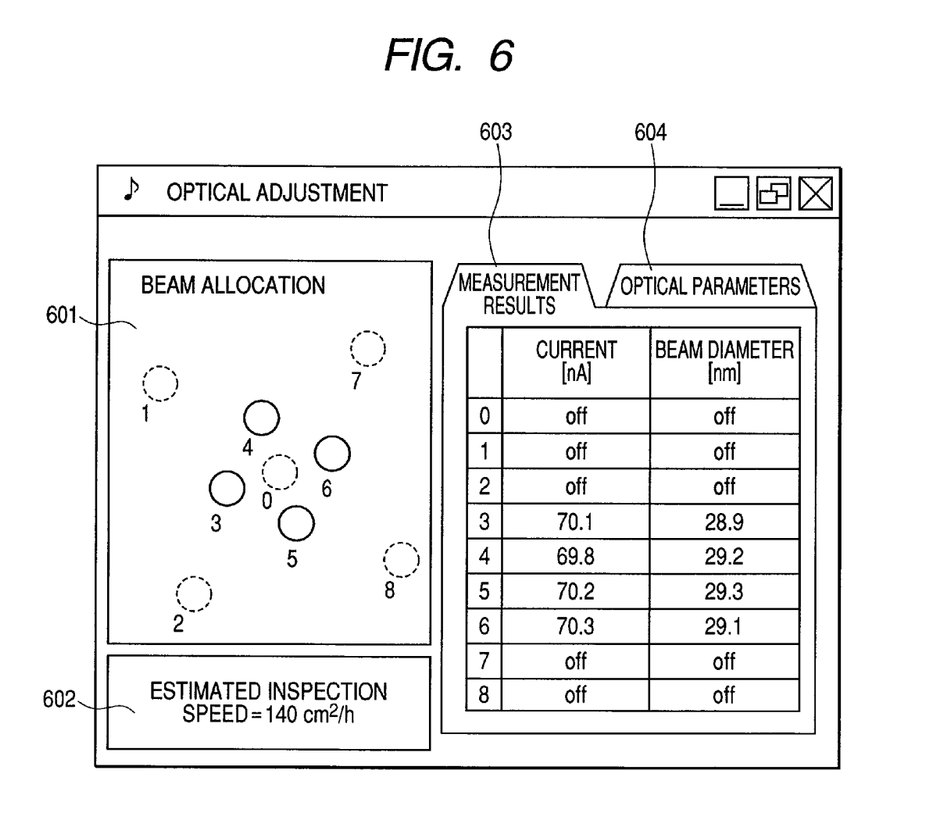
FIG. 6 is a window showing the results of the optical adjustment.

In step 512, optical adjustment is performed for the primary beams that entered in the optical system in the downstream side instep 511. By using the reference sample 132, the Faraday cup 133, and other devices that are mounted on the stage 117, the property of the primary beam such as the beam diameter and current are measured for each one of the N primary beams selected in step 511, and whether or not they become the desired values is confirmed. In addition, if the primary beam is estimated to be shifted for the electron optical system, the shift is corrected using the aligner (not shown in the figure). Furthermore, if the settings of the accelerating voltage (the electric potential difference between the cathode 101 and the anode 104) and the retarding voltage applied to the sample 116 were change in step 511, the operation conditions of the Wien filter is adjusted so that the primary beams go straight and the secondary beams are deflected to the direction of the detectors. After adjusting the optical system, the measurement results of the beam diameters and the currents before and after the correction are displayed on the image display unit 131 for the N primary beams. FIG. 6 shows an example of a display window for the measurement results after the correction. In this example, the beam allocation that the system control section 126 determined in step 510 is displayed in the beam allocation display area 601, and the inspection speed that the system control section 126 calculated in step 508 is displayed in the inspection speed display area 602 as the estimated inspection speed. When the operator click the Measurement results tab 603, the current and the beam diameter of the each primary beam on the sample is displayed. When the operator click the Optical parameter tab 604, every optical parameter such as the voltage applied to the aligner that is used in the correction is displayed. In addition, the beam diameters and the currents before and after the correction, and every optical parameter such as the voltage applied to the aligner are stored in the system control section 126 as the log data.

In step 513, the system control section 126 irradiates the primary beams, which are entered in the optical system in the downstream side in step 511, on the sample 116 or the reference sample 132, separates the generated secondary beams, and adjusts the voltage (or current) applied to the secondary beam axis adjustment aligner 121, and the focal length and other parameters of the secondary beam condenser lens 122 so that the secondary beams enter in the respective predetermined detectors. Furthermore, the system control section 126 adjusts the gain, offset, and other parameters of the amplifier circuits 124d and 124f, and fixes up the waveform of the signals input in the A/D converter 125.

In step 514, the specification window for the alignment is displayed on the image display unit 131, and when the operator specifies plural points in an alignment chip on the wafer through this window, the apparatus detects the alignment mark automatically, and corrects the stage coordinates for the wafer; that is, the alignment is executed.

In step 515, a trial inspection is carried out for a small region within a predetermined chip.

In step 516, the operator sets a threshold value of the image contrast to use it for judging defects based on the result of the trial inspection.

After setting the optimum threshold value, the operator clicks the Inspect button displayed on the image display unit 131 to start the actual inspection (step 517). The system control section 126 memorizes the time when the inspection is started, predicts the inspection finish time based on the inspection speed that is calculated in step 508, and displays the inspection finish time on the image display unit 131.

In addition, in the present embodiment, the system control section 126 calculated the value of every specification parameter and the estimated inspection speed for all the combinations of the optical parameters, the control parameters, and the beam allocations in step 508, and judged whether or not the each specification parameter calculated in step 508 satisfies the allowable conditions for each combination; however, to reduce the processing time furthermore, the parameters may be optimized in the order from the optical parameters or the control parameters that strongly affect the specification parameters to narrow down the range of the targets to search.

Furthermore, in the present embodiment, the system control section 126 selected the combination with the highest inspection speed in step 510; however, if a judgment formula in which the inspection speed and other specification parameters are combined is used, the optimization of the optical parameters, the control parameters, and the beam allocation can be performed by weighting the specified parameters.

Or, the system control section 126 leaves plural combinations as the candidates of the combinations in step 511, and the operator may determine the final optical parameters, control parameters, and the beam allocation using the image obtained from the trial inspection in step 516. Or, the operator or the system control section 126 may determine the final optical parameters, control parameters, and the beam allocation by selecting a combination that separates the difference between the normally formed pattern and the poorly formed pattern more effectively using the histogram of the brightness of every pixel of the image.

What is claimed is:

1. A multi-beam type electron beam inspection apparatus comprising:
    a primary optical system that separates a plurality of primary electron beams of a radiated electron beam from an electron source, and scans the plurality of primary electron beams on a sample:
    a detection system that detects secondary electron beams by the scanning of the plurality of primary electron beams, and outputs the detected secondary electron beams;
    a secondary optical system that directs the secondary electron beams corresponding to the plurality of primary electron beams to the detection system;
    a sample stage to move the sample table; and
    a control unit to control the primary optical system, the detection system, the secondary optical system, and the sample stage,
    wherein the control unit selects a number of the primary electron beams to irradiate the sample on the basis of the electric field intensity on the sample surface.

2. The multi-beam type electron beam inspection apparatus according to claim 1, further comprising:
    a unit to apply a retarding electric potential to the sample table,
    wherein the control unit selects the number of the primary electron beams to irradiate the sample on the basis of the retarding electric potential in substitution for the electric field intensity on the sample surface.

3. The multi-beam type electron beam inspection apparatus according to claim 2,
    wherein the control unit selects a distance of the primary electron beams on the basis of the retarding electric potential in substitution for the electric field intensity on the sample surface.

4. The multi-beam type electron beam inspection apparatus according to claim 1,
    wherein the control unit selects the number of the primary electron beams to irradiate the sample on the basis of an accelerating voltage of the primary optical system in substitution for the electric field intensity on the sample surface.

5. The multi-beam type electron beam inspection apparatus according to claim 4,
wherein the control unit selects a distance of the primary electron beams on the basis of an accelerating voltage of the primary optical system on the sample surface.

6. The multi-beam type electron beam inspection apparatus according to claim 1,
wherein the control unit selects a distance of the primary electron beams on the basis of the electric field intensity on the sample surface.

7. The multi-beam type electron beam inspection apparatus according to claim 1, further comprising:
a unit to apply a retarding electric potential to the sample table; and
an electrode to adjust the electric field intensity on the sample surface.

8. A multi-beam type electron beam inspection apparatus comprising:
a primary optical system that separates a plurality of primary electron beams of a radiated electron beam from an electron source, and scans the plurality of primary electron beams on a sample;
a detection system that detects secondary electron beams by the scanning the plurality of primary electron beams, and outputs the detected secondary electron beams;
a secondary optical system that directs each of the secondary electron beams corresponding to the plurality of primary electron beams to the detection system;
a sample stage to move the sample table; and
a control unit to control the primary optical system, the detection system, the secondary optical system, and the sample stage,
wherein the control unit selects a distance of the primary electron beams on the basis of the electric field intensity on the sample surface.

9. The multi-beam type electron beam inspection apparatus according to claim 8, further comprising:
a unit to apply a retarding electric potential to the sample table,
wherein the control unit selects distance of the primary electron beams on the basis of the retarding electric potential in substitution for the electric field intensity on the sample surface.

10. The multi-beam type electron beam inspection apparatus according to claim 8,
wherein the control unit selects distance of the primary electron beams on the basis of the retarding electric potential in substitution for the electric field intensity on the sample surface.

* * * * *